US010736497B2

(12) United States Patent
Nicolau et al.

(10) Patent No.: US 10,736,497 B2
(45) Date of Patent: Aug. 11, 2020

(54) ANATOMICAL SITE RELOCALISATION USING DUAL DATA SYNCHRONISATION

(71) Applicants: INSTITUT HOSPITALO-UNIVERSITAIRE DE CHIRURGIE MINI-INVASIVE GUIDEE PAR L'IMAGE, Strasbourg (FR); INSTITUT DE RECHERCHE SUR LES CANCERS DE L'APPAREIL DIGESTIF-IRCAD, Strasbourg (FR)

(72) Inventors: Stephane Nicolau, Kehl (DE); Anant Suraj Vemuri, Strasbourg (FR); Luc Soler, Wolfisheim (FR); Jacques Marescaux, Scharrachbergheim (FR)

(73) Assignees: INSTITUT HOSPITALO-UNIVERSITAIRE DE CHIRURGIE MINI-INVASIVE GUIDEE PAR L'IMAGE, Strasbourg (FR); INSTITUT DE RECHECHE SUR LES CANCERS DE L'APPAREIL DIGESTIF—IRCAD, Strasbourg (FR)

( * ) Notice: Subject to any disclaimer, the term of this patent is extended or adjusted under 35 U.S.C. 154(b) by 1280 days.

(21) Appl. No.: 14/774,516

(22) PCT Filed: Mar. 11, 2014

(86) PCT No.: PCT/IB2014/000838
§ 371 (c)(1),
(2) Date: Sep. 10, 2015

(87) PCT Pub. No.: WO2014/140813
PCT Pub. Date: Sep. 18, 2014

(65) Prior Publication Data
US 2016/0022125 A1  Jan. 28, 2016

Related U.S. Application Data

(60) Provisional application No. 61/775,930, filed on Mar. 11, 2013.

(51) Int. Cl.
*A61B 1/04* (2006.01)
*A61B 5/06* (2006.01)
(Continued)

(52) U.S. Cl.
CPC ............ *A61B 1/04* (2013.01); *A61B 1/00009* (2013.01); *A61B 1/0016* (2013.01); *A61B 5/062* (2013.01);
(Continued)

(58) Field of Classification Search
CPC ........... A61B 1/04; A61B 34/20; A61B 5/062; A61B 1/0016; A61B 1/00009;
(Continued)

(56) References Cited

U.S. PATENT DOCUMENTS 5,829,444 A * 11/1998 Ferre .................. A61B 5/06
128/897
7,397,364 B2 * 7/2008 Govari ................. A61B 5/06
340/13.27

(Continued)

OTHER PUBLICATIONS

Vemuri Anant Suraj et al. Basu Samik Sbasuiotaastate Edu Iowa State University Department of Computer Science 210 Atanasoff Hall 50: "Inter-operative Trajectory Registration for Endoluminal Video Synchronization: Application to Biopsy Site Re-localization", Sep. 22, 2013 (Sep. 22, 2013), p. 372-379, XP047041939, ISSN: 0302-9743 ISBN:978-3-642-45339-7.

(Continued)

*Primary Examiner* — Oommen Jacob
(74) *Attorney, Agent, or Firm* — Young & Thompson

(57) ABSTRACT

A method and a system for anatomical site relocalisation using dual data synchronisation. Method for repositioning, (Continued)

possibly several times, at a specific location, which has been already explored during a first or "reference exploration", a flexible endoscope during one or more successive endoluminal or extraluminal subsequent or "new exploration", or similar procedures, wherein the repositioning is realized either manually, by a human user, or automatically, by a robotic system, from or by way of a synchronisation process between a "new exploration" flexible endoscope video and the "reference exploration" flexible endoscope video displayed in parallel on or in two different windows, on one or more screens.

26 Claims, 10 Drawing Sheets
(4 of 10 Drawing Sheet(s) Filed in Color)

(51) Int. Cl.
*A61B 34/20* (2016.01)
*G06T 7/73* (2017.01)
*A61B 1/00* (2006.01)
*G06K 9/00* (2006.01)
*G06K 9/46* (2006.01)
*G06T 7/00* (2017.01)
*G06T 19/00* (2011.01)
*H04N 5/225* (2006.01)
*A61B 90/00* (2016.01)

(52) U.S. Cl.
CPC .......... *A61B 34/20* (2016.02); *G06K 9/00758* (2013.01); *G06K 9/4671* (2013.01); *G06T 7/0014* (2013.01); *G06T 7/74* (2017.01); *G06T 19/006* (2013.01); *H04N 5/2251* (2013.01); *A61B 2034/2051* (2016.02); *A61B 2034/2055* (2016.02); *A61B 2034/2065* (2016.02); *A61B 2090/364* (2016.02); *G06T 2207/30004* (2013.01)

(58) Field of Classification Search
CPC .... A61B 2034/2051; A61B 2034/2065; A61B 2090/364; A61B 2034/2055; G06T 7/74; G06T 19/006; G06T 7/0014; G06T 2207/30004; H04N 5/2251; G06K 9/4671; G06K 9/00758
See application file for complete search history.

(56) References Cited

U.S. PATENT DOCUMENTS

| | | | |
|---|---|---|---|
| 7,945,310 B2 | 5/2011 | Gattani et al. | |
| 2003/0197781 A1* | 10/2003 | Sugimoto | A61B 1/04 348/72 |
| 2005/0033149 A1 | 2/2005 | Strommer et al. | |
| 2005/0085718 A1 | 4/2005 | Shahidi | |
| 2005/0182295 A1* | 8/2005 | Soper | A61B 1/0008 600/117 |
| 2005/0228250 A1* | 10/2005 | Bitter | A61B 5/02007 600/407 |
| 2007/0055128 A1 | 3/2007 | Glossop | |
| 2008/0071143 A1* | 3/2008 | Gattani | A61B 1/00009 600/117 |
| 2008/0097155 A1* | 4/2008 | Gattani | A61B 1/00039 600/117 |
| 2008/0207997 A1* | 8/2008 | Higgins | A61B 1/00009 600/114 |
| 2011/0032347 A1* | 2/2011 | Lacey | A61B 1/00154 348/68 |
| 2011/0060189 A1* | 3/2011 | Belson | A61B 1/00158 600/117 |
| 2011/0230758 A1 | 9/2011 | Eichler | |
| 2011/0282151 A1* | 11/2011 | Trovato | A61B 5/06 600/117 |
| 2012/0062714 A1* | 3/2012 | Liu | G06T 7/75 348/65 |
| 2012/0069167 A1* | 3/2012 | Liu | A61B 6/584 348/65 |
| 2016/0022125 A1* | 1/2016 | Nicolau | A61B 5/062 600/424 |

OTHER PUBLICATIONS

Anant S. Vemuri et al: "Deformable three-dimensional model architecture for interactive augmented reality in minimally invasive surgery", Surgical Endoscopy, vol. 26, No. 12, Jun. 27, 2012 (Jun. 27, 2012), pp. 3655-3662, XP055128708, ISSN: 0930-2794, DOI: 10.1007/s00464-012-2395-0 the whole document.

International Search Report, dated Aug. 22, 2014, from corresponding PCT application.

* cited by examiner

ANATOMICAL SITE RELOCALISATION USING DUAL DATA SYNCHRONISATION

FIELD OF THE INVENTION

The present invention concerns a method and a system for repositioning quickly and precisely at a specific location already explored a flexible endoscope (or a similar medical device) during successive endoluminal or extraluminal exploration or similar procedures (after partial or total extraction) performed on a body of a subject.

The localisation and tracking of biopsy sites inter-operatively poses a significant challenge for providing targeted treatments. This invention provides a guided navigation to the medical operator or surgeon for accurate re-positioning of a flexible endoscope at previously targeted sites.

The invention concerns more specifically target sites located in more or less flexible tubular organs of subjects, or at least tube like elongated passages within the bodies of such subjects.

Primarily, but not limitatively, envisaged organs are the oesophagus and the colon.

BACKGROUND OF THE INVENTION

In relation to the field of the invention of the first preferred mentioned implementation, it is known that oesophageal adenocarcinoma (OAC) is rapidly increasing in frequency in the United States and other western countries. Gastroesophageal reflux disease, a benign complication caused by the stomach acid coming into the oesophagus, as a chronic condition, leads to Barrett's oesophagus (BE). It refers to the metaplasia in the cells of the lower oesophagus and in most cases is a precursor to OAC. The evolution of BE to an adenocarcinoma is observed to progress from low-grade to a high-grade dysplasia.

Medical guidelines prescribe different levels of surveillance intervals depending on the degree of dysplasia with a minimum of two biopsies per year. A typical surveillance procedure involves taking four quadrant biopsies every 2 cm towards the distal end of the oesophagus and in suspicious regions. The biopsied tissue is sent to the pathology for evaluation. With the introduction of devices such as the probe-based confocal laser endomicroscopy real-time visualization and diagnosis of suspected regions can be performed intera-operatively. High resolution narrow band imaging has also been used for diagnosis and surveillance by visual inspection of the mucosa and the subepithelium.

In each of these cases, during a follow-up inspection, the gastro-intestinal (GI) specialist is required to locate the previously biopsied or surveyed location. This problem in the literature has been termed as the re-localisation issue. Typically, the GI specialist uses the printed markings on the endoscope (commonly one mark every 5 or 10 cm along the flexible body), which can be highly unreliable and which limit his or her ability to accurately re-position the endoscope and the optical biopsy probe and hence to effectively track the disease. Due to the lack of deterministic tools for providing such re-localisation inter-operatively, the GI specialist has to survey or biopsy the entire affected oesophagus region, which prevents targeted treatments.

To the inventors' knowledge, there is no previous work or proposal which tackles this issue of re-localisation of the flexible endoscope inter-operatively. However, several approaches to track biopsy points intra-operatively exist: Baptiste Allain et al. Biopsy site re-localisation based on the computation of epipolar lines from two previous endoscopic images. In International Conference on Medical Image Computing and Computer-Assisted Intervention (MICCAI), volume 12, pages 491-8. Springer, Heidelberg, January 2009; Peter Mountney et al. Optical biopsy mapping for minimally invasive cancer screening. In International Conference on Medical Image Computing and Computer Assisted Intervention (MICCAI), volume 12, pages 483-90. Springer, Heidelberg, January 2009; Baptiste Allain et al. A system for biopsy site re-targeting with uncertainty in gastroenterology and oropharyngeal examinations. In International Conference on Medical Image Computing and Computer-Assisted Intervention (MICCAI), volume 13, pages 514-21, January 2010.

Each of them relies on the recovery of the 3D structure of the anatomy, to map and track the biopsy sites as they move in and out of the field-of-view of the endoscope frame. These known solutions either employ epipolar geometry or propose a simultaneous localisation and mapping (SLAM) based method. Selen Atasoy et al. ("Probabilistic region matching in narrow-band endoscopy for targeted optical biopsy". In International Conference on Medical Image Computing and Computer-Assisted Intervention (MICCAI), volume 12, pages 499-506. Springer, Heidelberg, January 2009) propose a probabilistic region matching approach in narrow-band images by using feature matches obtained from affine invariant anisotropic feature detector.

More recently Selen Atasoy et al. ("Endoscopic video manifolds for targeted optical biopsy". IEEE transactions on medical imaging, 31(3):637-53, March 2012) propose to formulate the re-localisation as image-manifold learning process. By projecting endoscopic images on low dimensional space they propose to classify and cluster the images collected during multiple interventions into manageable segments, which they claim would aid in re-localisation of the biopsy sites. However, they do not provide any spatial relations of the extracted segments inter-operatively, and so have not sufficiently clarified the application of their result in a clinical context for re-localisation.

The inventors are of the opinion that, relying only on image based information for information extraction, that has to be mapped across multiple interventions can be highly unreliable; especially, due to temporal changes in tissue texture over multiple procedures, coupled with a highly deformable endoscopic scene, where repeatability of feature extraction, matching and tracking poses a significant challenge.

Additional methods and systems allowing to position an instrument or an endoscope within a human body are also known from the prior art, such as from U.S. Pat. No. 7,945,310, US 2005/0085718 and US 2007/0055128.

Nevertheless, these other known solutions rely on preoperative virtual 2D or 3D images, provided by an external imaging system.

These solutions thus require an important preliminary data treatment and cannot take changes in tissue texture or deformation of the targeted scene or of the environment of said scene into account.

SUMMARY OF THE INVENTION

It is an aim of the present invention to overcome the limitations of the previously quoted prior art.

To that end, the main object of the invention is a method for repositioning, possibly several times, at a specific location, which has been already explored during a first or "reference exploration", a flexible endoscope during one or more successive endoluminal or extraluminal subsequent or "new exploration", or similar procedures, wherein the repositioning is realized either manually, by a human user, or automatically, by a robotic system, from or by means of a synchronisation process between a "new exploration" flexible endoscope video and the "reference exploration" flexible endoscope video displayed in parallel on or in two different windows, on one or more screens.

Herein, the terms "first", "previous" or "reference" in relation to exploration, intervention or procedure have equivalent meanings and refer to an exploration, an intervention or a procedure which has normally been performed previously (in time) to a "new", "subsequent" or "current" exploration, intervention or procedure of the same type, and whose data have been recorded and stored (totally or partially only).

The new, subsequent or current exploration, intervention or procedure can be a live (real-time current) one or an exploration, intervention or procedure also based on recorded data, and therefore not necessarily performed later in time.

Preferably, the synchronisation process is based only on the position and possibly orientation registration of the end tip of the flexible endoscope recorded during the first or reference exploration and a subsequent or new exploration from a tracking device, providing the location and orientation of said end tip of the endoscope according to a fixed external reference frame such as an electro-magnetic, fiberoptic or any other similar type of tracking device.

Thus, by attaching for example an electromagnetic (EM) sensor to the tip of a flexible endoscope, its movement within the body can be tracked with respect to a fixed external reference frame. By computing the correspondence between the EM sensor positions in two successive interventions, a guided-view is provided to the GI specialist. This guided-view consists of a matching image extracted from the previously recorded intervention that best matches the subsequent, for example live viewed intervention.

Alternately, the synchronisation process can be based on the position and orientation registration of the end tip of the flexible endoscope recorded during the first or reference exploration and a subsequent or new exploration from a tracking device, improved by a real-time endoscopic video analysis, performing an extraction and a matching of similar features visible during both the first or reference exploration and the subsequent or new exploration.

In connection with this embodiment, one can consider using feature descriptor to improve synchronisation.

A basic implementation can rely on a simple algorithm to perform the video synchronisation. This algorithm uses only the recorded position and orientation of a 6 DOF sensor of the previous exploration and the live position and orientation of said sensor during the subsequent exploration. In case the oesophagus or similar tubular organ undergoes some deformation, or in case the registration step is inaccurate, the synchronisation algorithm can be improved and made more robust using image analysis according to a state-of-the-art technique. For instance, feature descriptors can be recorded for each recorded images of the previous exploration, such as the ones disclosed in: David G. Lowe, "Distinctive Image Features from Scale-Invariant Keypoints", International Journal of Computer Vision, vol. 60, No. 2, 2004, p. 91-110 or in: Herbert Bay, Andreas Ess, Tinne Tuytelaars, Luc Van Gool, "SURF: Speeded Up Robust Features", Computer Vision and Image Understanding (CVIU), vol. 110, No. 3, p. 346-359, 2008. Then, during the subsequent exploration, the best feature descriptors can be extracted from the live image and matched to a subset of images from the previous exploration, which are close (in term of distance) to the image that has been selected using the sensor position and orientation information only. Obviously, any kind of feature descriptor can be used for this purpose. An analysis of the number of matched descriptors and the matching quality can thus be used to select an image that looks more similar than the one originally selected from the sensor position and orientation information only.

Advantageously, the two synchronised flexible endoscopic videos are enhanced by virtual tags indicating specific points of interest, these virtual tags being defined on the first or reference exploration flexible endoscopic video interactively by the user and in the subsequent or new exploration flexible endoscopic video automatically thanks to image analysis based on the comparison of the two synchronized videos.

Alternately, the two synchronised flexible endoscopic video can be enhanced by virtual tags indicating specific points of interest, these virtual tags being defined on the first or reference exploration flexible endoscopic video automatically by an automatic video image analysis extracting visible points of interest, such as for example anatomical, pathological or surgical specific features, and in the subsequent or new exploration flexible endoscopic video automatically thanks to image analysis combining a comparison algorithm of the two synchronized videos with an automatic video image analysis extracting the same visible points of interest in the subsequent or new exploration flexible endoscopic video.

For example, in relation to the previous embodiment, one can consider using image analysis and feature descriptor to perform auto-tagging of biopsy sites in the reference exploration and the new exploration.

Since the entire reference exploration can be recorded, it also contains the step of biopsies during which an instrument is inserted in one of the endoscope operating channel to cut and retrieve a tissue sample (or to perform an optical sample using confocal microscopy device from Maunakea Technology). State-of-the art image analysis allows tracking instrument position in the video image as disclosed in: Allan, M., Ourselin, S., Thompson, S., Hawkes, D. J., Kelly, J., Stoyanov, D. (2013). Toward detection and localization of instruments in minimally invasive surgery. IEEE Trans Biomed Eng 60(4), 1050-1058. Thus, if the instrument size and camera calibration are known, its 3D position with respect to the camera frame is also known. This means that the biopsy position can be automatically computed in the tracking (EM) frame from the analysis of the reference exploration video, provided that the position of the camera frame with respect to the sensor (EM) frame (attached to its tip) has been previously calibrated (using for instance the method described in F. Dornaika and R. Horaud. Simultaneous robot-world and hand-eye calibration. Robotics and Automation, IEEE Transactions on, 14(4):617-622, 1998).

Once the biopsy sites have all been tagged in the reference exploration, it is then possible using feature descriptor to estimate their position in the new exploration. Indeed, a first step of feature descriptor detection can be performed in the reference exploration frames that contain the biopsy sites. Then, for each biopsy site identified in an image with pixel coordinate (u,v), its relative position with respect to the detected descriptors in the same image is recorded. Afterwards, descriptors are detected in the new exploration frames and matched to the ones of the reference exploration. For all frames $F_{exp}$ in the new exploration that contain at least three descriptors matched with the descriptors of the frame containing a biopsy, it is possible to estimate the pixel biopsy position in $F_{exp}$ using registration techniques. There are many possibilities for this registration step. Use of barycentric coordinate is a standard choice when three descriptors have been matched. However, homography registration may be more relevant in case at least four descriptors have been found around the biopsy site (homography allows modelling perspective distortion using four or more points).

According to a possible embodiment of the invention, the two synchronised flexible endoscopic videos, enhanced or not by virtual tags indicating specific points of interest, are fused using augmented reality techniques with a virtual rendering of the body 3D models of the anatomical and/or pathological structure, this 3D models being extracted from a preoperative medical image realized before the subsequent or new exploration of the body of the subject.

Adding augmented reality information in the new exploration images from preoperative 3D model can, for example, be performed as described hereinafter.

In case a preoperative image or the patient is available (typically a 3D CT-scan or MRI image), it is possible to compute the link (rotation+translation) between the preoperative image frame $F_{preop}$ and the (EM) tracking system frame FEM. This computation can be performed using, for instance, the oesophagus central line extracted manually or automatically from the preoperative image in $F_{preop}$ and registered to the oesophagus trajectory estimated during the new exploration in $F_{EM}$. In this context, the oesophagus trajectory must contain, in both frames, the transition point between oesophagus and stomach, and a part of the throat.

In the case two EM markers are stuck on the patient chest, it is easy to manually or automatically extract from preoperative image in $F_{preop}$ the two points that anatomically correspond to the two EM markers and one point in the oesophagus. These three points can then be used as described previously to register the frame $F_{preop}$ and $F_{EM}$.

Once the relative position of $F_{preop}$ and $F_{EM}$ is known, it is straight forward to superimpose information extracted from the preoperative image (3D surface model or volume rendering) in the endoscopic video frame, provided that the position of the camera frame with respect to the EM sensor frame (attached to its tip) has been previously calibrated (using for instance the method described in: F. Dornaika and R. Horaud. Simultaneous robot-world and hand-eye calibration. Robotics and Automation, IEEE Transactions on, 14(4):617-622, 1998.

The synchronisation process of the method of the invention can be more precisely composed of the following three processing steps:

First step: recording the location of the flexible endoscope end tip using a tracking system providing the location and orientation of the end tip of the endoscope according to a fixed external reference frame such as an electro-magnetic, fiberoptic or similar tracking device, and the associated flexible endoscope video during the endoluminal or extraluminal first or reference exploration.

Second step: processing, in particular registering, the location of the flexible endoscope end tip using a tracking system providing the location and orientation of the end tip of the endoscope according to a fixed external reference frame such as an electro-magnetic, fiberoptic or similar tracking device), and the associated flexible endoscope video during an endoluminal or extraluminal subsequent or new exploration.

Third step synchronizing the subsequent or new exploration video and the first or reference exploration video from or using the registration of the flexible endoscope end tip location between the real-time subsequent exploration and the first exploration.

The following (1 to 3) partial alternate embodiments of one or several steps of the synchronisation process described before can be envisaged:

1) The third step of the synchronisation comprises synchronizing the subsequent or new exploration video and the first or reference exploration video from or by means of a registration of the flexible endoscope end tip location between the real-time exploration and the reference exploration, improved by a real-time flexible endoscopic video analysis extracting and matching similar feature(s) visible in both first reference exploration and real-time subsequent exploration.

2) The synchronisation process is more precisely composed of the following four step process:

First step as described before.

Second step: adding an interactive virtual tagging of one of more images of the first or reference exploration flexible endoscopic video indicating specific points of interest in the body of the explored subject, this virtual tagging being realized from a specific first or reference exploration video reader allowing to add tags in any selected image of the video through any interaction or human interface device allowing to precisely select a pixel or group of pixels in a video, such as by mouse, pad, trackball, joystick or optical tracking.

Third step: equivalent or identical to the second step described earlier.

Fourth step: performing the third step described earlier (three step process), the registration process being improved by adding an analysis of the subsequent or new exploration video localizing in this video the same specific points of interest in the body of the explored subject tagged in the second step, and adding it in the same location on the synchronised subsequent or new exploration video, with a superimposition of these virtual tags.

3) The synchronisation process is more precisely composed of the following four step process:

First step: the same first step as mentioned before.

Second step: adding an automatic virtual tagging on one or more images of the first or reference exploration flexible endoscopic video, indicating specific points of interest in the body of the explored subject, this virtual tagging being preferably realized automatically through specific video analysis algorithm, for instance based on color, brightness, contrast and textures analysis as well as on features tracking, extracting visible points of interest, such as anatomical, pathological or surgical specific features.

Third step: equivalent or identical to the second step mentioned before (three step process).

Fourth step: performing the third step mentioned before (three step process), the registration process being improved by adding an analysis of the subsequent new exploration video, localizing in this video the same specific point of interest in the body of the explored subject tagged in the second step, and adding it in the same location on the synchronised subsequent new exploration video, a superimposition of these virtual tags, the same algorithm of point of interest detection used in the second step being possibly combined with other registration algorithms as defined in the third step described before (three step process).

As a typical application of the invention, the exploration with the flexible endoscope is performed in a tubular organ of a human subject, such as the oesophagus or the colon.

The method according to the invention can be performed without the use of any additional marker, if the position of the subject remains unchanged or can be approximately reproduced between the previous and the subsequent explorations.

Nevertheless, if this is not the case, the invention can foresee that at least two markers, whose positions can be recorded with the used tracking system or an other tracking system, are previously placed on given anatomical locations on the subject, said locations depending on the explored tubular organ and preferably not undergoing noticeable deformation or displacement when the subject changes position, are used to provide referential points in the previous and subsequent explorations, preferably together with at least one other internal easily identifiable anatomical point.

To increase the accuracy of the relocation, the referential points can be used to define and attach a frame or referential to the subject in the first and subsequent explorations.

In order to limit the needed computation resources and to speed up the relocation process, the synchronisation process according to the invention can be focused on the terminal exploration phase, i.e. when the tip of the endoscope approaches the region of interest. Thus, during a first or previous exploration, a limited number of images are recorded or selected, which contain the relevant information, preferably marked or tagged, and wherein, during the subsequent exploration, the video image processing and synchronizing step is performed, and guidance information provided, only when the current or live endoscope position is close to the position associated with images containing the relevant information.

According to an other feature of the invention, when a tubular organ is explored, an image processing is performed which analyses the lumen position in the video image during the subsequent exploration and selects the image from the previous exploration associated to a position close to the subsequent live position with a similar lumen position.

Advantageously, when the explored organ is the colon, the three points or parts of the colon which are known to be attached to the abdominal wall are used as fixed reference points or locations, the reaching of a target during a subsequent exploration being preferably performed through backward motion.

The relocation process can also take into account, when needed, the rotation of the endoscope. Thus, the orientation of the tip of the flexible endoscope is recorded, and exploited, in addition to its 3D position, by the tracking system, to evaluate the rotation difference of the endoscope orientation between the reference and the subsequent exploration.

When considering the invention from a practical point of view, one can consider that the precise relocation of the tip of the flexible endoscope is performed through two consecutive operational steps:

a gross localisation, by performing an approximate positioning of the tip of the flexible endoscope close to a reference point or position, such as a biopsy site, determined in a previously conducted procedure, as described before;

a fine positioning, by referring to a mapping of the target site or points, taken during a previous procedure onto the video images in the subsequent or current intervention.

The invention also encompasses a medical system able to perform the method described herein before.

BRIEF DESCRIPTION OF THE DRAWINGS

The patent or application file contains at least one drawing executed in color. Copies of this patent or patent application publication with color drawings will be provided by the Patent and Trademark Office upon request and payment of the necessary fee.

The invention will be better understood thanks to the following description and drawings of embodiments of said invention given as non limitative examples thereof.

In the accompanying drawings:

FIGS. 1 and 2 are similar schematic views of a medical system comprising a flexible endoscope and a tracking system according to two embodiments of the invention, during the exploration of a human oesophagus;

FIGS. 3A, 3B and 3C are three synoptic functional views illustrating the three main steps of the relocation method according to a preferred embodiment of the invention;

Figure 4:
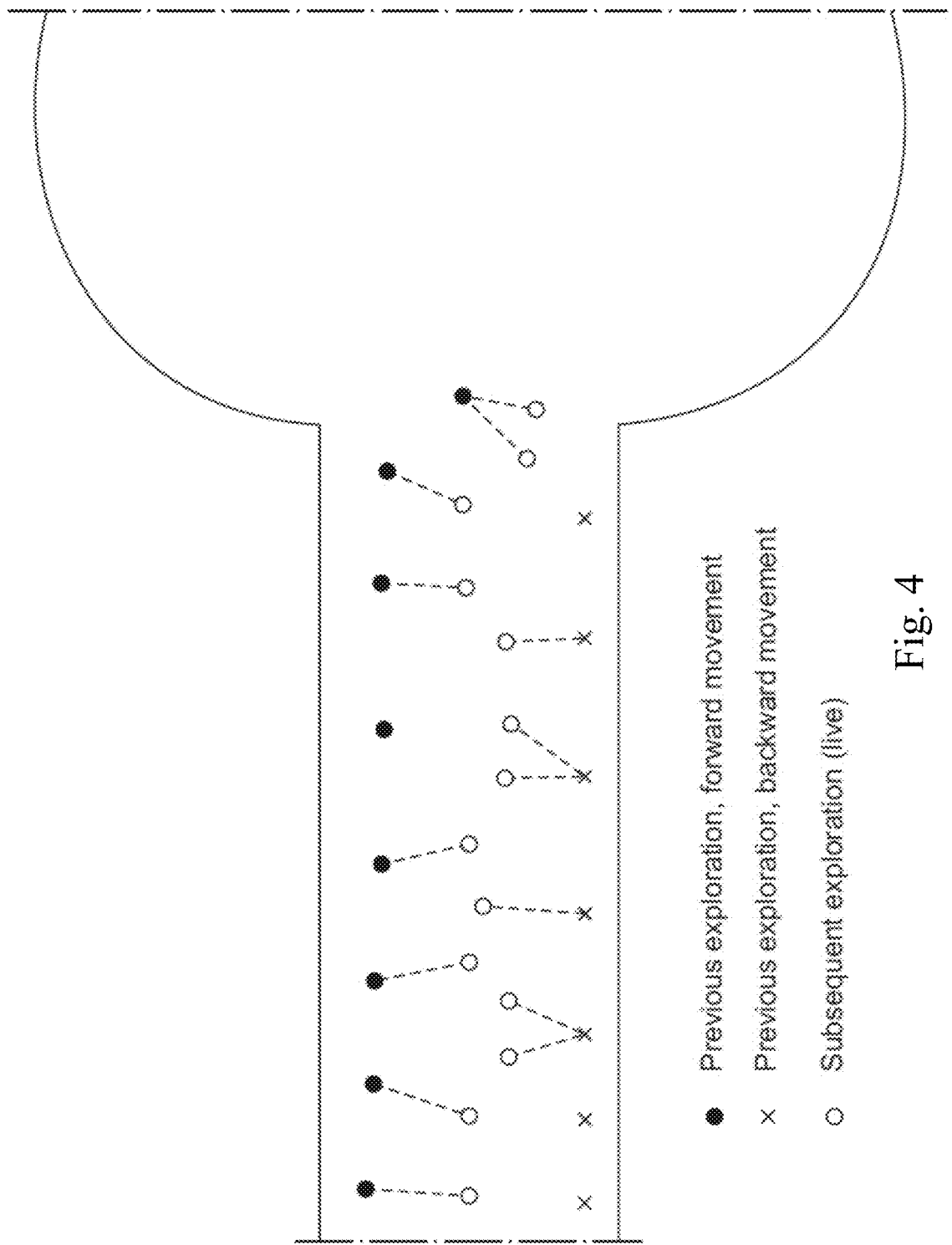
Figure 5:
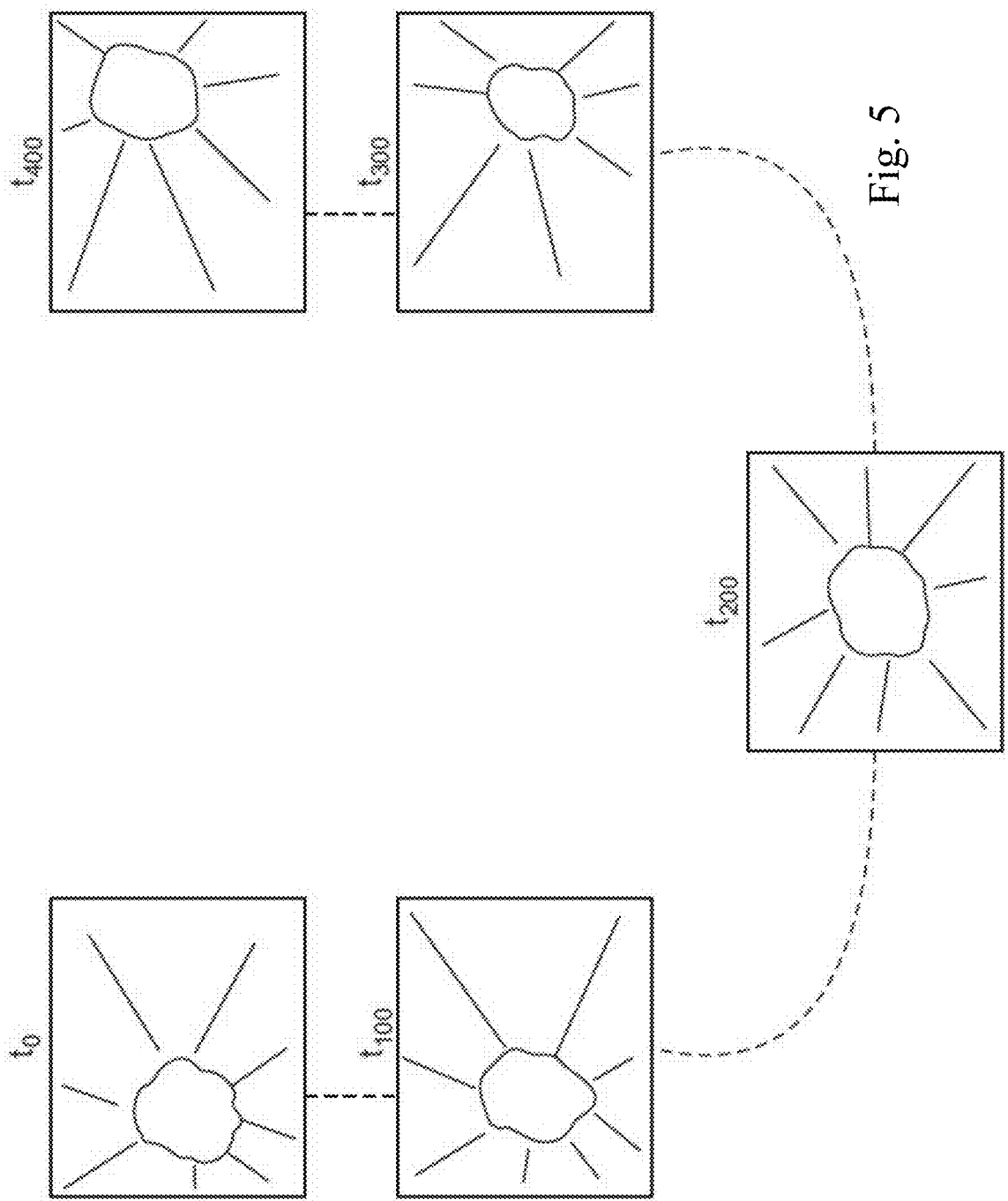
Figure 6:
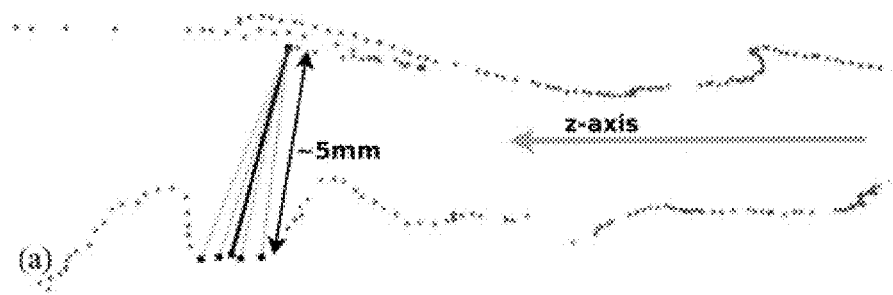
Figure 7:
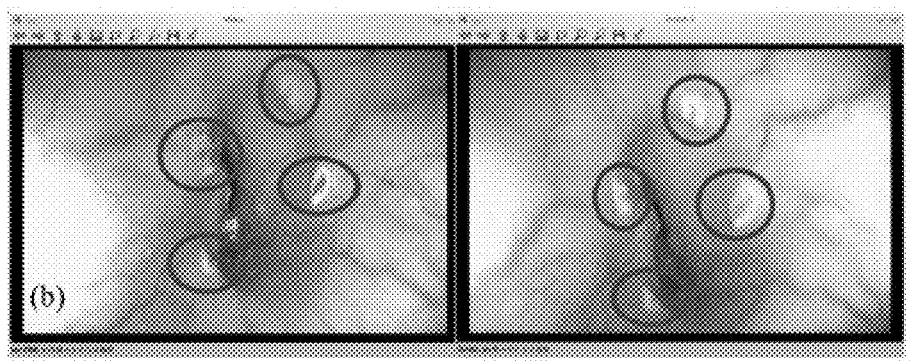
Figure 8:
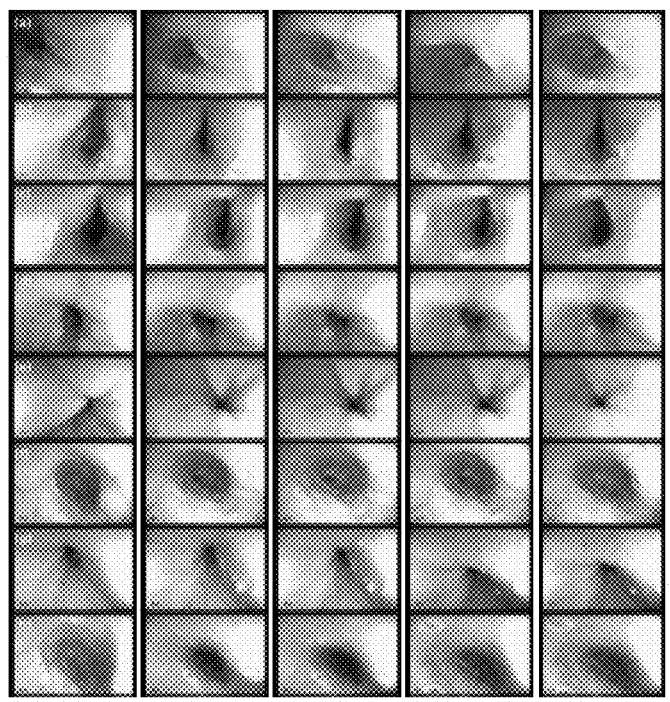
Figure 9:
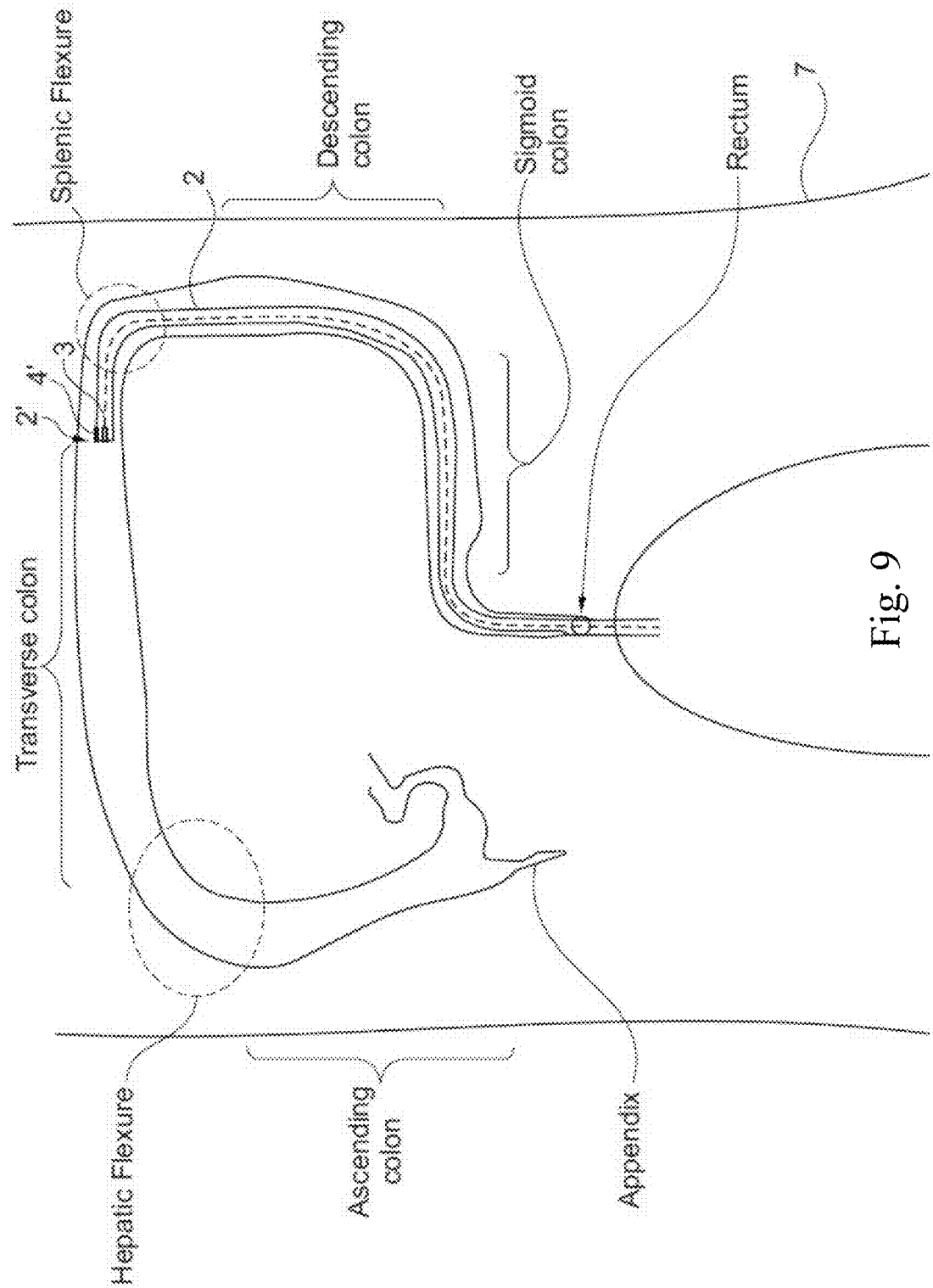
Figure 10A:
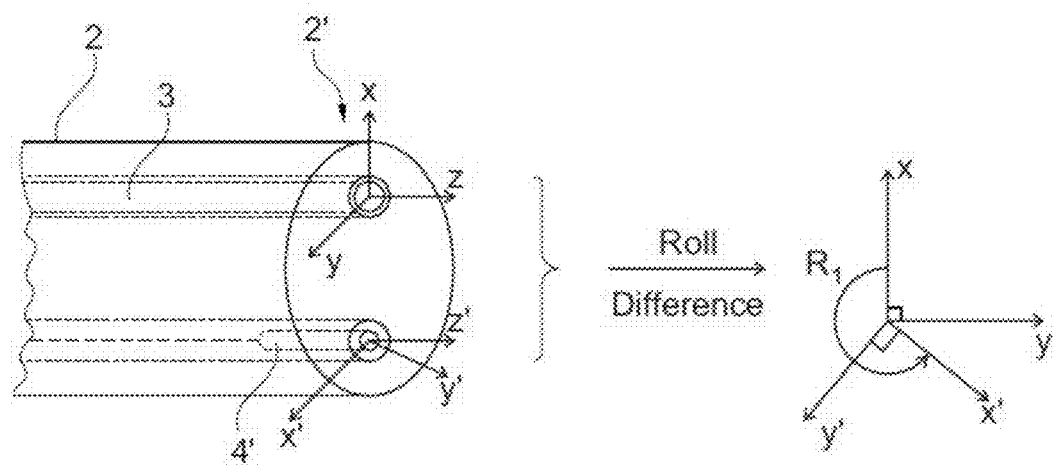
Figure 10B:
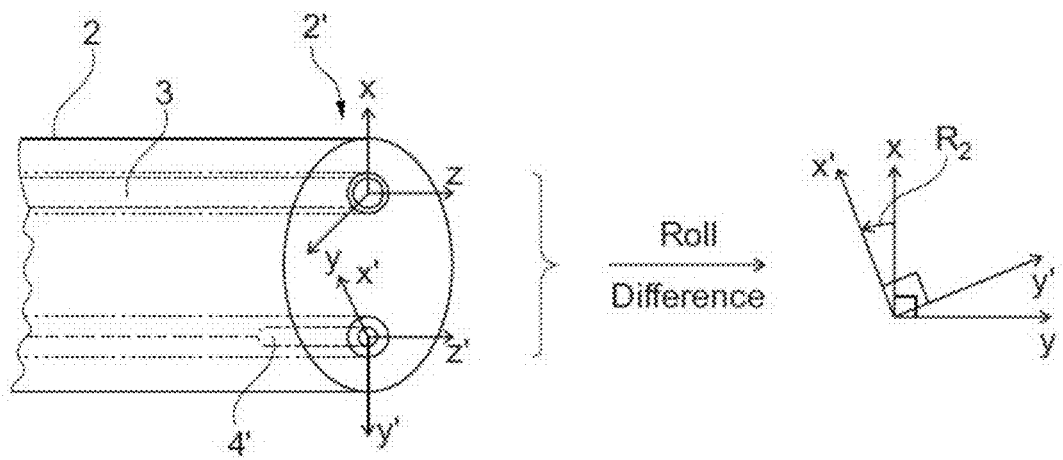

FIG. 4 is a partial schematic representation illustrating the different trajectories (successive positions) of the tip of a flexible endoscope during the forward movement of a first or previous exploration, during the backward movement of said first or previous exploration and during a subsequent, for example live, exploration of a tubular organ, for example the oesophagus. Dotted lines between subsequent exploration positions and previous exploration positions correspond to synchronisation process based on Euclidean distance: given a position from the subsequent exploration, the video frame displayed from the previous exploration is the one associated to the closest position from the previous exploration;

FIG. 5 shows images of a lumen taken during a forward exploration and during a backward exploration performed according to FIG. 4;

FIG. 6 illustrates the previously and subsequent live trajectories of the tip of the flexible endoscope within an oesophagus and the corresponding matches;

FIG. 7 shows images of the live view (left) and of the best matched image from a previously recorded exploration (right), the encircled regions indicating markings made by using a thermal burn tool of the endoscope;

FIG. 8 shows multiple endoscopic images arranged in columns, wherein the first column shows the frames from the live video, the second column shows the closest match, column 3, 4 and 5 presenting frames randomly selected from the 20 best matches obtained from the synchronisation process;

FIG. 9 is a schematical view of the colon of a human body subjected to an exploration by a flexible endoscope (partially shown), and, FIGS. 10A and 10B are partial schematic views of the end part (tip) of the flexible endoscope, illustrating the calibration and compensation in roll during a first or previous exploration (FIG. 10A) and a subsequent or current exploration (FIG. 10B—referential x, y, z is attached to the camera lense and referential x', y', z' is attached to the sensor).

DETAILED DESCRIPTION OF THE INVENTION

Figure 1:
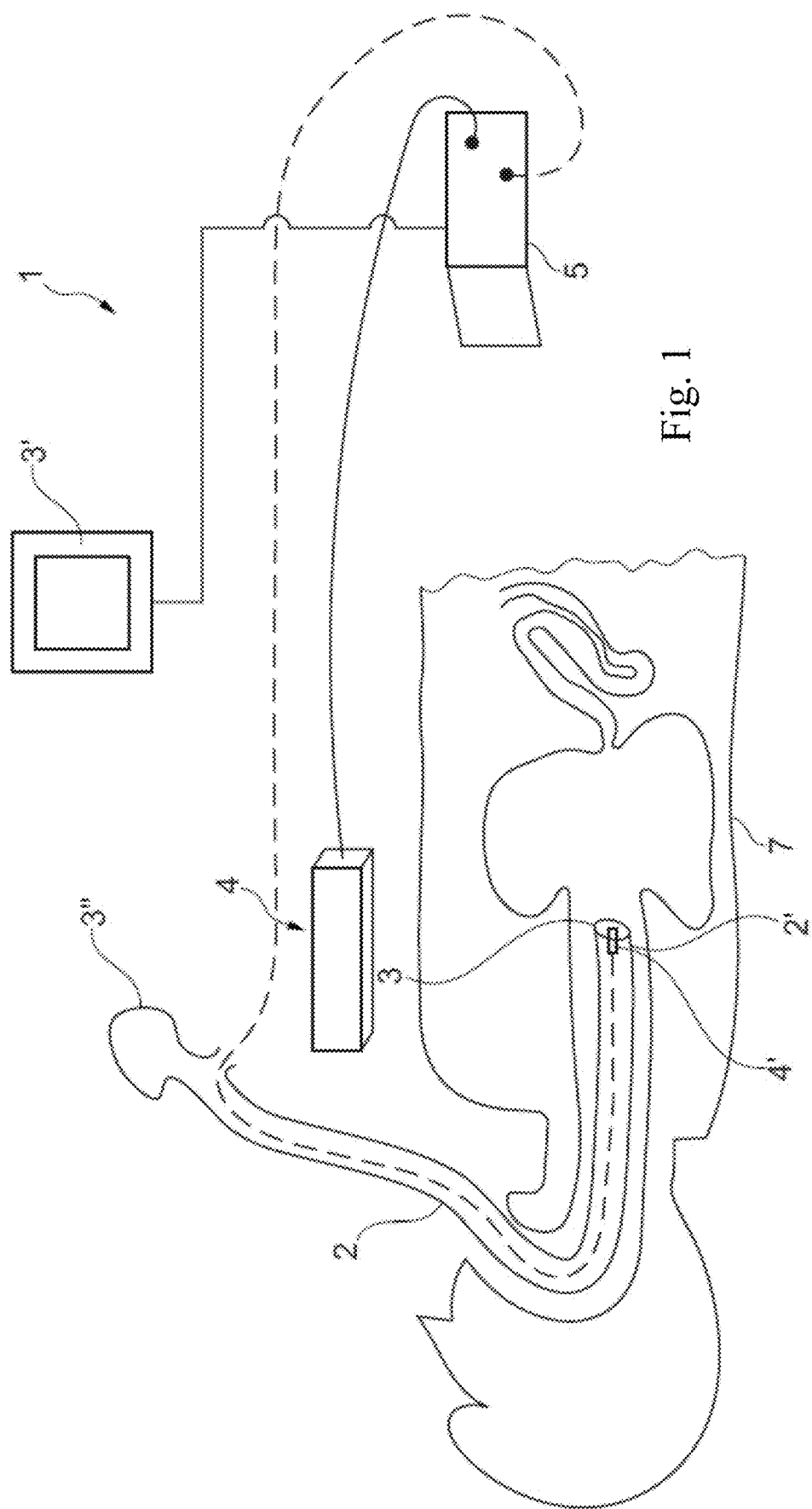
Figure 2:
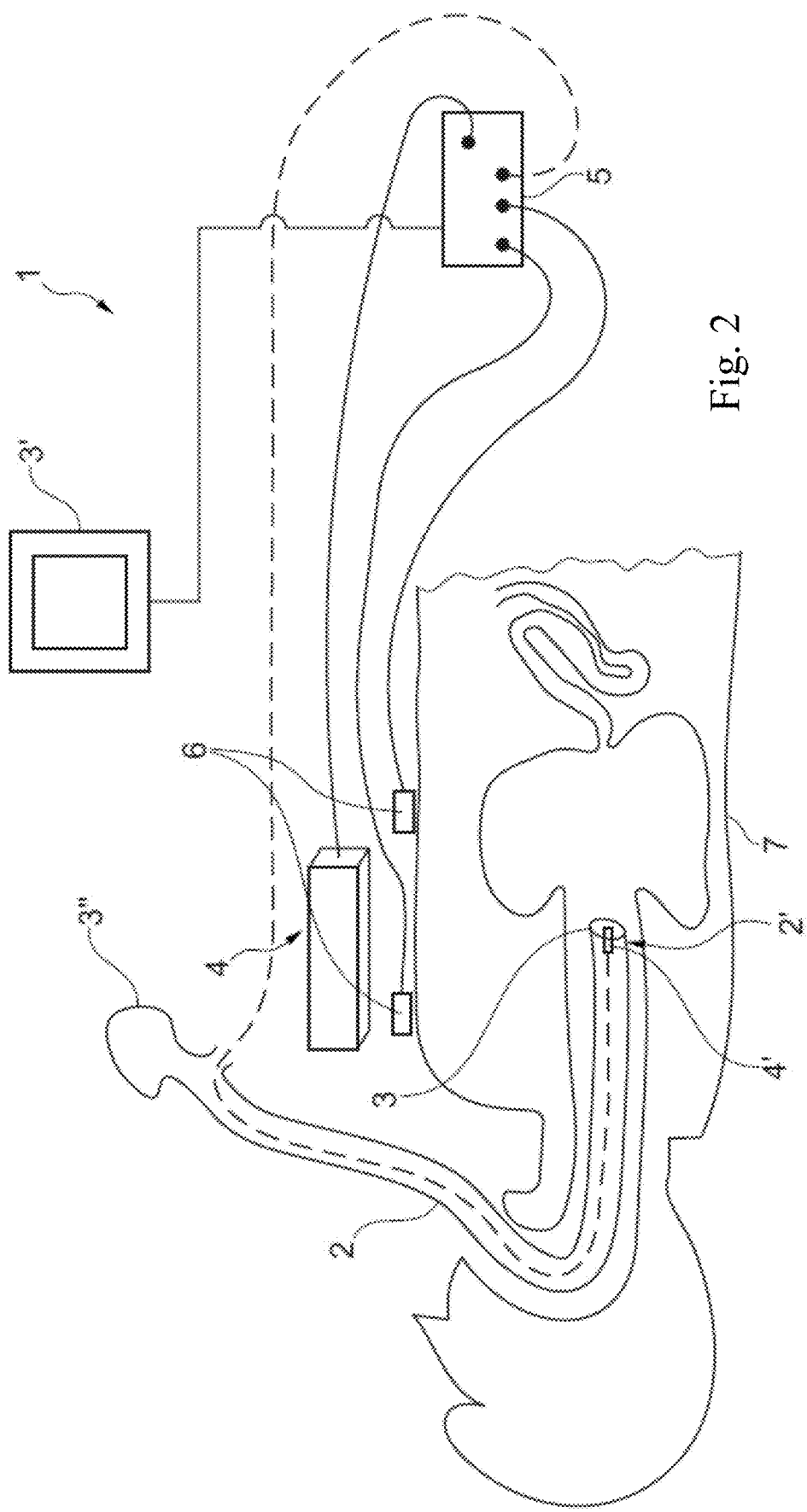

FIGS. 1 and 2, and partially FIG. 9, show a medical system 1 according to the invention, comprising a flexible endoscope 2 which can be introduced in a tubular organ of a subject 7, and able to be used for performing the method according to the invention.

More precisely, said medical system 1 mainly comprises:

i) a flexible endoscope 2 at least equipped with an image taking device 3, and possibly at least one tool or instrument, ii) display 3' and movement control 3" means associated with said endoscope 3, iii) a tracking device or system 4 providing the location and orientation of the end tip 2' of the endoscope 2, such as an electromagnetic tracking device or a flexible optical tracking device, iiii) computer means 5 and associated storing means, wherein the frontal or end tip 2' of the endoscope 2 is provided with an electromagnetic sensor 4' or a similar tracking device and said medical system 1 further comprises means, in particular software means within the computer means 5, able to perform the method as described before.

The sensor 4' affixed to or mounted into the tip 2' of the flexible endoscope 2 and the corresponding tracking system 4 allows at least a 3D position tracking, preferably also an orientation tracking of said tip.

According to a first implementation of the inventive system and as illustrated in FIG. 1, no external marker (for instance electromagnetic or optical) is needed to perform the registration between the EM frame during a previous exploration and the EM frame during a subsequent exploration. Indeed, the method can fully rely on the throat and oesophagus shape estimation, which is performed during the previous and subsequent exploration. However, for this technique to be efficient, the patient head orientation with respect to the shoulder during the previous and subsequent exploration should be approximately the same and the medical expert has to reach the stomach entry point, which can possibly be constraining or not feasible for some patient (for instance in case of oesophagus obstruction due to a big tumor in the middle of the oesophagus).

In order to solve this issue, the invention can make use of additional markers 6 presented hereafter and illustrated in FIG. 2. More precisely, it can be based on the use of at least two supplementary EM markers which are stuck on the patient chest, preferably along the sternum, on anatomical points that can be easily found back, and which do not undergo important deformation in case the patient has not the same position during the previous and subsequent exploration (the patient can lay on the supine position and then on a decubitus lateral). It has been found that the jugular notch was a remarkably static anatomical point, as well as the sternum end point.

In this context, during the previous exploration, preferably the two markers 6 are stuck on the patient 7 during the intervention and their positions are recorded as well. The recorded position can be either only one acquisition for both points, or a collection of acquisitions for each marker which is averaged since it is assumed that the patient should not move during the intervention. Then, during the subsequent exploration, two markers 6 are stuck on the patient 7 at approximately the same anatomical positions, and their positions are recorded. A first approach to perform the registration is then to do a 3D/3D point registration (see Arun K S, Huang T S, Blostein S D. "Least-squares fitting of two 3-d point sets. In IEEE Transactions on Pattern Analysis and Machine Intelligence". 1987 May; 9(5):698-700) using two point triplets identified during each exploration. This triplet can be the two marker positions and the point $P_{closest}$ on the oesophagus shape estimation (it is approximately a collection of point with a line shape, curved close to the patient's throat), which is the closest to the marker stuck on the jugular notch.

However, the inventors noticed that there is some uncertainty in finding repetitively the sternum end point (along the sternum). Additionally, the inventors also observed that the relative position of the closest point $P_{closest}$ to the jugular notch can change between the previous and the subsequent exploration of several millimeters. The 3D/3D registration may thus not be very accurate and it is proposed instead to register the following frame F that can be defined during the previous and subsequent exploration. The frame F center is defined by the marker stuck on the jugular notch, its X axis is defined by the vector $M_jM_s$ between the jugular notch marker and the sternum end point marker, its Y axis is defined by the cross product between $M_jM_s$ and the vector between the jugular notch marker and $P_{closest}$, its Z axis being then computed from the cross product between X and Y axis. The expert in the field will easily understand that registering the two frames instead of the two point triplets dramatically diminishes the influence of the uncertainty of the sternum marker position and of $P_{closest}$ on the registration result.

The invention basically aims at displaying a frame from the previous exploration, which point of view in the oesophagus or similar tubular organ is as close as possible to the point of view of the live/subsequent exploration. Finding the most adapted frame can be computationally expensive. A simpler implementation is possible, which still provides a guidance tool for medical experts but uses only a small or reduced collection of recorded image frames.

During the previous exploration phase, the medical expert annotates the images that he considers relevant. Let assume there are about 50 relevant images $R_i$, i belonging to the range [1-50] (containing for instance biopsy information or pathology information), on which he indicates the position of the relevant information (an arrow or a circle can be superimposed on the image to show the relevant information). During the subsequent exploration, the system will show the live images of the subsequent exploration on one screen, and display the relevant images $R_i$ only if the live endoscope position is close to the position associated to the relevant images $R_i$ after the registration step (for instance, if the distance between the endoscope position and the position associated to $R_i$ is within a threshold value, say 3 mm) The system can also indicate in which direction (forward or backward) the endoscope should be moved to get closer to the point associated to $R_i$. This indication can be provided by means of an oriented arrow, a letter (for instance, F or B) or a color indicator.

The invention can also consider the issue of dealing with unsmooth positions of recorded frames.

Obviously, it can happen that several relevant images are associated to points, which are very close, thus separated by a distance below the threshold value. In this case, the system can display all relevant images in a mosaic representation on a screen, or the system may ask the medical expert, which relevant image among the several relevant images he wants to reach.

During the previous exploration, the system repetitively and simultaneously records the endoscope position via the (EM) sensor associated to the corresponding image during the procedure. It is thus possible that many pairs position+ image are recorded for a specific depth in the oesophagus or similar tubular organ, but with a different lateral position of the endoscope in said organ. In this case, and as described later herein, a basic approach to select, during the subsequent live exploration, the image from the previous exploration corresponding to the current position of the endoscope may be uncomfortable for the medical expert. Indeed, the displayed images at time t may be very different from the image at time t+1, the point of view of the endoscope in the oesophagus or similar tubular organ being very different: the image flow is then not smooth. This phenomenon typically arises when the medical expert has recorded the entire forth and back exploration and is illustrated on FIG. 4. As can be seen on FIG. 5, the lumen can be on the left side of the video images during the forward motion of the endoscope ($t_0$-$t_{200}$) and on the right side of the video images during the backward motion of the endoscope ($t_{200}$-$t_{400}$), within the same exploration procedure.

This phenomenon can also arise when multiple biopsies are performed at similar depth but on opposite sides of the organ. In order to solve this problem, an image processing approach can be adopted, which analyses the lumen position in the image at time t and selects the image from previous exploration associated to a position close to the live position with a similar lumen position, as illustrated in FIG. 5.

Another issue which can be addressed by the invention is taking the rotation of the endoscope into account.

Indeed, during the subsequent exploration, the medical expert introduces the endoscope with an orientation around its axis (usually called roll) that may be different from the orientation during the previous exploration. An experienced medical expert is usually able, by watching some specific marks on the endoscope, to approximately have the same orientation between the previous and the subsequent exploration. However, this takes time and is not so easy for a novice medical expert. If the orientation of the endoscope is not the same, the method can of course synchronize the two exploration videos but the image orientation will not be the same, and thus it will be less easy for the medical expert to recognize the same anatomical structure in both videos.

On this point, the inventive method can be improved to compute the live orientation error between the previous exploration and the subsequent exploration. Once the orientation error is computed, the system can indicate with an arrow on the live video screen in which direction the endoscope should be rotated so that the rotation error is reduced. The rotation error in degree can also be displayed and updated.

Once the orientation error is computed, the system can also apply automatically the rotation that compensates the error to the previous exploration video, or to the subsequent exploration video.

Hereafter, it is explained, by way of example, how the live orientation error between the previous and the subsequent exploration can be computed. To track the flexible endoscope tip inside the oesophagus or similar tubular organ, a 6 DOF electromagnetic sensor is set at the tip of the endoscope. The recording step during the previous exploration includes not only the 3D position of the endoscope tip, but also its orientation (roll, yaw and pitch). During the subsequent exploration, the orientation of the endoscope tip is also acquired.

The two following cases can occur:

If the relative orientation between the camera and the 6DOF sensor at the endoscope tip is the same during the previous exploration and during the subsequent exploration (i.e. the endoscope that has been used during the previous exploration is the same than during the subsequent exploration, or the endoscope manufacturer guarantees that each produced endoscope has the same relative orientation between the camera and the 6 DOF sensor at the endoscope tip), the orientation error can be given by the roll difference between the 6 DOF sensor orientation of the live endoscope position and the recorded 6 DOF sensor orientation at the position from the previous exploration that has been matched to the live endoscope position.

If, on the contrary, the relative orientation between the camera and the 6 DOF sensor at the endoscope tip is not the same during the previous exploration and during the subsequent exploration, a preliminary calibration step is necessary in order to compute the roll difference R1 between the endoscopic camera frame (which z axis is commonly chosen along the camera point of view) and the 6 DOF sensor frame (which z axis is usually along EM sensor coil, thus almost parallel to camera z axis in this context) during the previous exploration and the roll difference R2 between the endoscopic camera frame and the 6 DOF sensor frame during the subsequent exploration (this is illustrated by FIGS. 10A and 10B). The difference between R1 and R2 then allows simulating that the same endoscope with the same relative position between the camera and the 6 DOF sensor has been used during the previous and the subsequent exploration. The method described in the previous paragraph can thus be applied successfully.

A practical embodiment of the invention, in relation to oesophagus explorations, will now be described more precisely by way of example.

The system setup 1 consists of an EM field generator 4 with an adapted working volume which is placed roughly above the chest of the patient 7 and fixed in position using a titanium arm. A 6 DOF EM sensor 4' is inserted into the working channel of the flexible endoscope 2 and fixed at the tip 2' of the endoscope. The EMTS and the endoscope 2 are connected to a laptop or similar computer concerns 5, that synchronously records the data. A recording of an intervention consists of a list of EM sensor poses (trajectory of the endoscope tip 2'), with the corresponding image frames captured from the endoscope 2. During a possible live subsequent procedure, given the recording of a previously conducted intervention, a corresponding image can be found in the recording, that spatially matches the endoscope's current location in the oesophagus.

Figure 3A:
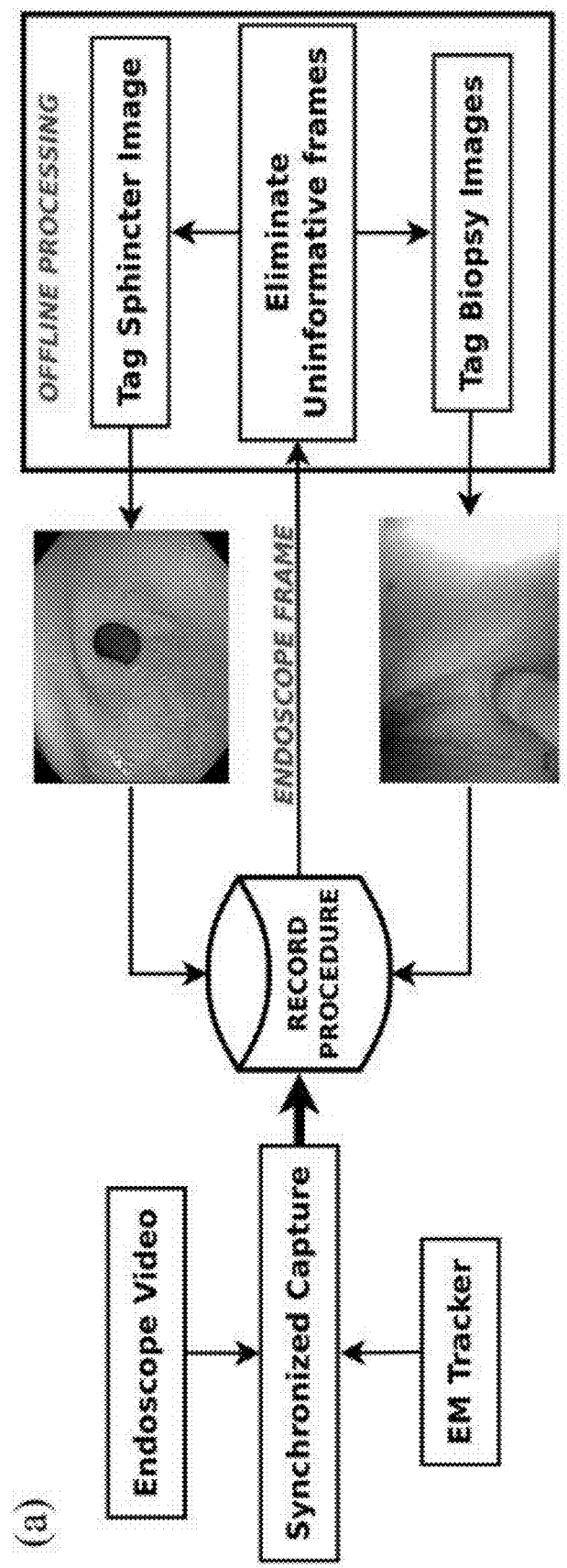
Figure 3B:
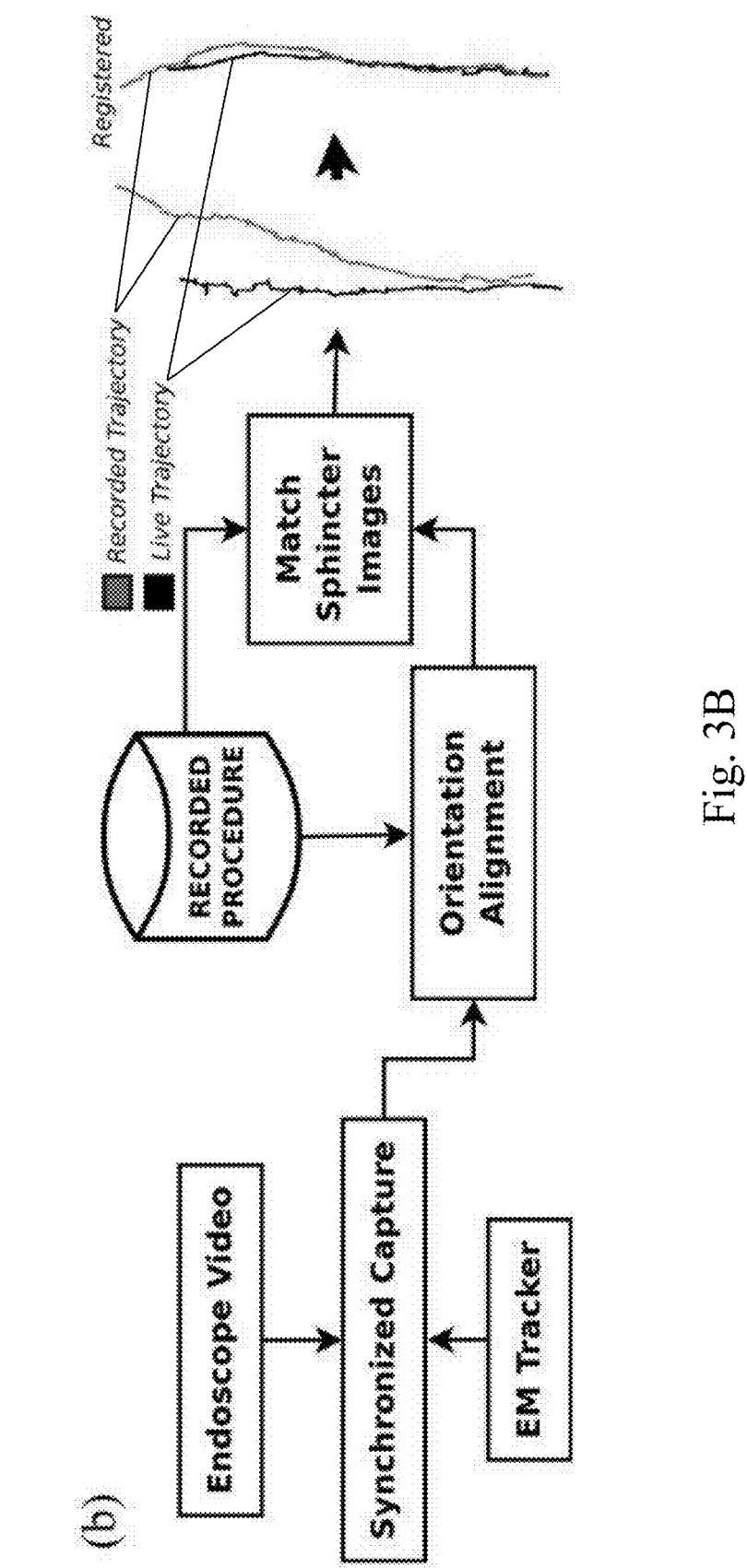
Figure 3C:
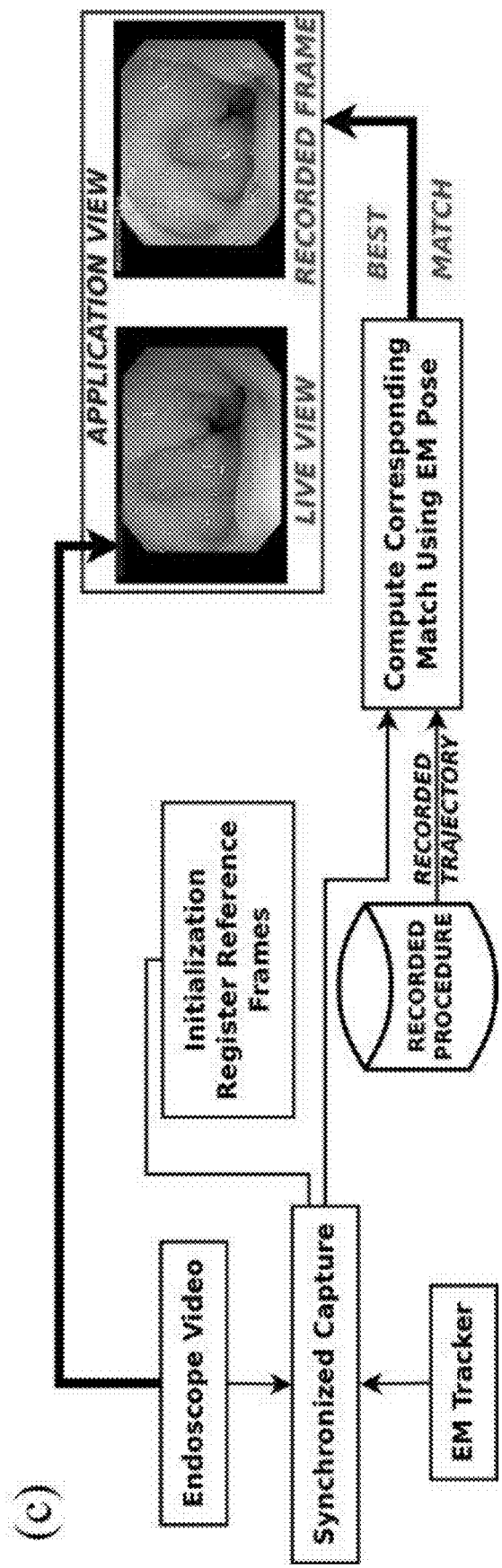

FIGS. 3A to 3C provide an overview of the work-flow of the inventive method. The used process is divided into three parts or phases:

Acquisition phase: in which the recorded data is tagged and stored for further processing;

Registration phase: to perform registration of EMTS reference frames of the live procedure and a previously recorded intervention chosen for providing a guided view, and Synchronisation phase: to perform spatial synchronisation between the trajectories of the live intervention and the recording that was previously registered.

The acquisition phase is schematically illustrated on FIG. 3A.

During this phase, the GI specialist performs the recording of an intervention and tagging of relevant images. The flexible endoscope is slowly guided through the oesophagus, while the EM sensor pose and the corresponding image acquired from the endoscope are recorded to the database. The recording contains many uninformative frames; with bubbles, motion-blur, specular highlights, and out-of-focus images. Firstly, these uninformative frames are detected and left out from further processing using the method described in: M K Bashar et al. Automatic detection of information frames from wireless capsule endoscopy images. Medical image analysis, 14(3):449-70, June 201. The GI specialist tags the images containing the sphincter as it is used as a landmark in the registration phase. The sphincter is used as the anatomical landmark because it is stable and can be reached with good repeatable accuracy. The endoscopic frames that contain the biopsy procedure are tagged and in an offline step, the expert reviews the tagged biopsy images and selects those most relevant for the procedure. At this stage, the expert can choose to add supplementary information to the images of the recordings, which will be available during the synchronisation phase.

The registration phase is illustrated on FIG. 3B.

Since the set-up of the EMTS would always change inter-operatively, registration must be performed between the EMTS reference frames of the live intervention and a recording of a previous intervention chosen for providing a guided-view. Preferably, an on-line registration is used, without introducing additional constraints in the operating room. To achieve this, firstly, the EM sensor position is recorded while the GI specialist introduces the endoscope into the oesophagus and guides it until the sphincter. The contextual knowledge that the oesophagus is fairly linear and exhibits very minimal lateral movement is used. Hence, the largest principal components of the live trajectory and the trajectory of the previous intervention can be used to obtain 3D orientation alignment along vector $z=[001]^T$ for each trajectory. The tagged sphincter positions can then be used to obtain translation t, which along with R provides an initialisation for the iterative closest point (ICP) for further registration refinement.

The synchronisation phase is illustrated on FIG. 3C.

Once the reference frames have been aligned, a spatial correspondence between the sensor position from the current intervention and the previously recorded intervention is computed. By partitioning the trajectory of the previous intervention as a binary tree, a search for the closest neighbour (in Euclidean sense) to the current sensor position is made. Due to localized deformations of the oesophagus during navigation, the trajectories are not smooth and exhibit deviations (FIG. 6) from the central oesophagus line (connecting the throat to the sphincter, along vector z), which can lead to a false match with marked depth difference. Since the trajectories have been aligned along vector z, the search space is constrained to lie within $\Delta z$ (approximately 2 mm) The closest neighbour gives the corresponding best matching image of the region in the oesophagus taken during the previous procedure. In particular, the matched images that were tagged to contain locations of biopsy sites, provide the GI specialist a more localized region for review. FIG. 7 resents the result of the synchronisation phase. ICP finds the transform up to a rotation along vector z, however, since the search space is constrained along this direction, the determination of the closet neighbour is unaffected by it.

The inventors performed experiments based on the inventive method and system, using NDI \copyright Aurora EMTS (accuracy of 0.5 mm in the given working volume).

The inventive method was tested on three sets of in-vivo sequences on different porcines, with each set consisting of four recordings. Prior marking were made on the oesophagus using a dual knife at every 2 cm to simulate biopsy locations. To replicate realistic surgical procedures conducted at different times, the EM field emitter was randomly repositioned before each recording. The steps described previously were performed, with the first recording as the reference and three other recordings to mimic a follow-up procedure. A qualitative evaluation of the approach was performed by presenting the output of the synchronisation phase to five experts.

As shown in FIG. 7, two images were presented, one displaying frames to emulate the live stream from an intervention and the second, displaying the corresponding matching frame from a previously recorded intervention. Using the markings made by the dual knife and other visible landmarks as reference, the expert assessed the relevance and quality of the matched image presented using our approach. The feedback of their experience was quantified. The evaluation experiment clearly shows that the experts found the inventive system very useful for re-localizing the simulated biopsy sites. However, it was suggested that the matched image did not necessarily provide the ideal viewpoint (FIG. 8, results a, b and e). Upon added investigation, the inventors observed that by considering the 20 best neighbours, the selection of best image can be refined to accommodate the best viewpoint. FIG. 8 shows a sample of these frames.

This approach already provides the GI specialist with a more advanced guidance, but the frame selection can be further improved by performing image analysis on these best neighbours.

The previous description of exemplary practical embodiments of the invention relies more specifically on applications on oesophagus.

Now, as also indicated previously, the invention method and system can also be used and applied to reposition or relocate quickly and precisely, at specific locations already explored, a flexible endoscope in other tubular more or less deformable organs.

This is for example the case with the colon which is known to be highly extensible and deformable, and also not at all straight in shape.

Due to this specific features of the colon, the inventive method takes into consideration the following information about anatomy of the colon: there exist three parts of the colon which are attached to abdominal wall, and thus which can be considered as reference landmarks: the right and the left colic flexures, the caecum to intestine transition. Since these three parts can be easily recognized by the medical expert, and their position recorded during explorations (previous and subsequent), it is then possible to map the size of each intermediate trajectory in the previous exploration to the corresponding one in the subsequent exploration. The medical expert (operator) firstly reaches the three fixed points in the current exploration, and the computer matches the three colon parts by applying a ratio to the length of each part, so that the length of each matched part in previous and subsequent exploration have the same value. Then, the medical expert can reach the relevant sites annotated or recorded during the previous exploration by slightly removing the endoscope until the inventive method indicates that he is close to the relevant sites. It is important to highlight that if the medical expert tries to reach a target using the inventive method by moving forward in the colon, it is likely that the information provided by the system may not be accurate. Indeed, it is well known that the unpredictable elastic deformation of the colon mainly occurs during the forward motion and much less during the backward motion.

As it results from the foregoing specification, the invention proposes a method and a system which are quite straightforward, work in real-time (trajectory matching at 50 to 100 Hz), can be used with minimal change to the operating room protocol and most of the offline steps can easily be automated. Moreover, because the system is scalable in time, the recordings can be shared between GI specialists without loss of information. Finally, since the inventive method does not rely on the quality of images, it is robust to typical endoscopic image artefacts for interoperative comparison.

The present invention is, of course, not limited to the preferred embodiments described and represented herein, changes can be made or equivalents used without departing from the scope of the invention.

The invention claimed is:

1. A medical system enabling a manual or automatic repositioning of a flexible endoscope at a specific location during at least one new exploration subsequent to a first or reference exploration during which said specific location in a tubular, at least partially deformable organ has already been explored by said endoscope, said medical system comprising:
   a flexible endoscope at least equipped with an image taking device;
   a display and movement controller associated with said endoscope;
   an end tip tracking device or system providing a 3D position and orientation of an end tip of the endoscope, which is affixed to or mounted into the end tip of the flexible endoscope; and
   a computer and associated storage, the storage being configured to store a reference exploration video acquired through the flexible endoscope during the first or reference exploration during which the specific location in the tubular, at least partially deformable organ has already been explored by the endoscope,
   wherein each of a plurality of captured video images captured during the new exploration and the reference exploration is associated with a respective synchronously-recorded endoscope tip 3D position and orientation,
   wherein the medical system is configured to:
      compute a spatial correspondence between at least one of the endoscope 3D tip positions of the new or subsequent exploration and at least one of the endoscope 3D tip positions of the reference exploration,
      search for a spatially closest neighbor image of the reference exploration video that is spatially closest to the specific location during the new exploration as a best matching image of the first or reference exploration, and
      display, in parallel on or in two different windows on one or more screens, a live image of a new or subsequent exploration video acquired through the flexible endoscope during the new exploration and the best matching image of the reference exploration video.

2. The medical system according to claim 1, further comprising at least two markers, whose positions are recordable with the end tip tracking device or system or a marker tracking system separate from the end tip tracking device or system, the at least one markers being configured to be placed on given anatomical locations on the subject having the tubular organ, said anatomical locations depending on the explored tubular organ and not undergoing noticeable deformation or displacement when the subject changes position, said markers providing referential points in the previous and subsequent explorations.

3. The medical system according to claim 1, further comprising one or more processors configured to provide real-time endoscopic video analysis, perform an extraction and a matching of similar features visible during both the first or reference exploration and the subsequent or new exploration.

4. The medical system according to claim 1, further comprising a human interface device configured to receive an input to precisely select a pixel or a group of pixels in a video, in order to perform an interactive virtual tagging of one or more images of the first or reference exploration flexible endoscopic video indicating specific points of interest in the body of the explored subject, the virtual tagging being realized from a specific reference exploration video reader that receives input to add tags in any selected image of the video.

5. The medical system according to claim 1, further comprising one or more processors configured to execute a video analysis algorithm to extract visible points of interest, the visible points of interest being anatomical, pathological or surgical specific features in the body of the explored subject and to realize an automatic virtual tagging on one or more images of the reference exploration flexible endoscopic video, indicating said specific points of interest.

6. The medical system according to claim 4, further comprising one or more processors configured to analyze the subsequent new exploration video, in order to localize in the subsequent new exploration video the same specific point of interest in the body of the explored subject tagged in an image of the reference exploration video, and to add the same specific point of interest in the same location on the synchronized subsequent new exploration video, with a superimposition of the virtual tags.

7. The medical system according to claim 1, further comprising one or more processors configured to fuse two synchronized flexible endoscopic videos, enhanced or not by virtual tags indicating specific points of interest, using augmented reality techniques with a virtual rendering of the body 3D models of the anatomical and/or pathological structure, the 3D models being extracted from a preoperative medical image realized before the new exploration of the body of the subject.

8. The medical system according to claim 1, wherein the flexible endoscope is further equipped with at least one tool or instrument, and
   the tracking device or system is an electromagnetic tracking device or a fiberoptic tracking device.

9. A method for repositioning, realized by the medical system according to claim 1, one or more times, at the specific location, which has previously been explored during the first or reference exploration, the flexible endoscope during one or more successive endoluminal or extraluminal subsequent explorations of the at least one new exploration the method comprising:
   synchronizing, by a synchronization process between a subsequent exploration flexible endoscope video and a reference exploration flexible endoscope video displayed in parallel on or in two different windows, on one or more screens.

10. The method according to claim 9, wherein the synchronization process is based only on the position and orientation registration of the end tip of the flexible endoscope recorded during the first or reference exploration and the subsequent or new exploration from the tracking device, providing the location and orientation of said end tip of the endoscope according to a fixed external reference frame.

11. The method according to claim 9, wherein the synchronization process is based on the position and orientation registration of the end tip of the flexible endoscope recorded during the reference exploration and the subsequent or new exploration from the tracking device or system, improved by a real-time endoscopic video analysis, performing an extraction and a matching of similar features visible during both the first or reference exploration and the subsequent or new exploration.

12. The method according to claim 9, wherein the two synchronized flexible endoscopic videos are enhanced by virtual tags indicating specific points of interest, the virtual tags being defined on the first or reference exploration flexible endoscopic video interactively by a user and in the subsequent or new exploration flexible endoscopic video automatically due to image analysis based on the comparison of the two synchronized videos.

13. The method according to claim 9, wherein the two synchronized flexible endoscopic videos are enhanced by virtual tags indicating specific points of interest, the virtual tags being defined on the first or reference exploration flexible endoscopic video automatically by an automatic video image analysis extracting visible points of interest including anatomical, pathological or surgical specific features, and in the subsequent or new exploration flexible endoscopic video automatically due to image analysis combining a comparison algorithm of the two synchronized videos with an automatic video image analysis extracting the same visible points of interest in the subsequent or new exploration flexible endoscopic video.

14. The method according to claim 9, wherein the two synchronized flexible endoscopic videos, enhanced or not by virtual tags indicating specific points of interest, are fused using augmented reality techniques with a virtual rendering of body 3D models of an anatomical and/or pathological structure, the 3D models being extracted from a preoperative medical image realized before the subsequent or new exploration of the body of the subject.

15. The method according to claim 10, wherein the synchronization process comprises:
   recording the location of the flexible endoscope end tip using a tracking system providing the location and orientation of the end tip of the endoscope according to a fixed external reference frame such as an electromagnetic, fiberoptic or similar tracking device, and the associated flexible endoscope video during the endoluminal or extraluminal first or reference exploration,
   registering the location of the flexible endoscope end tip using the end tip tracking device or system providing the location and orientation of the end tip of the endoscope according to a fixed external reference frame, and the associated flexible endoscope video during an endoluminal or extraluminal subsequent or new exploration, and
   synchronizing the subsequent or new exploration video and the first or reference exploration video from or using the registration of the flexible endoscope end tip location between the real-time subsequent exploration and the first exploration.

16. The method according to claim 15, wherein the synchronizing comprises synchronizing the subsequent or new exploration video and the first or reference exploration video from or by a registration of the flexible endoscope end tip location between the real-time exploration and the reference exploration, improved by a real-time flexible endoscopic video analysis extracting and matching one or more similar features visible in both first reference exploration and real-time subsequent exploration.

17. The method according to claim 15, wherein the synchronization comprises:
   recording the location of the flexible endoscope end tip using the end tip tracking device or system providing the location and orientation of the end tip of the endoscope according to a fixed external reference frame, and the associated flexible endoscope video during the endoluminal or extraluminal first or reference exploration,
   adding an interactive virtual tagging of one of more images of the first or reference exploration flexible endoscopic video indicating specific points of interest in the body of the explored subject, the virtual tagging being realized from a specific first or reference exploration video reader that allows a user to add tags in any selected image of the video through any interaction or human interface device that allows the user to precisely select a pixel or a group of pixels in a video,
   registering the location of the flexible endoscope end tip using the end tip tracking device or system providing the location and orientation of the end tip of the endoscope according to a fixed external reference frame, and the associated flexible endoscope video during an endoluminal or extraluminal subsequent or new exploration, and
   synchronizing the subsequent or new exploration video and the first or reference exploration video from or using the registration of the flexible endoscope end tip location between the real-time subsequent exploration and the first exploration, the registration process being improved by adding an analysis of the subsequent or new exploration video localizing in the subsequent or new exploration video the same specific points of interest in the body of the tagged explored subject, and adding the analysis in the same location on the synchronized subsequent or new exploration video, with a superimposition of the virtual tags.

18. The method according to claim 15, wherein the synchronization process comprises:
   recording the location of the flexible endoscope end tip using the end tip tracking device or system providing the location and orientation of the end tip of the endoscope according to a fixed external reference frame, and the associated flexible endoscope video during the endoluminal or extraluminal first or reference exploration,
   adding an automatic virtual tagging on one or more images of the first or reference exploration flexible endoscopic video, indicating specific points of interest in the body of the explored subject, the virtual tagging being preferably realized automatically through a specific video analysis algorithm, based on one or more of color, brightness, contrast, and textures analysis and based on features tracking, extracting visible points of interest,
   registering the location of the flexible endoscope end tip using the end tip tracking device or system providing the location and orientation of the end tip of the endoscope according to a fixed external reference frame, and the associated flexible endoscope video during an endoluminal or extraluminal subsequent or new exploration, and
   synchronizing the subsequent or new exploration video and the first or reference exploration video from or using the registration of the flexible endoscope end tip location between the real-time subsequent exploration and the first exploration, the registration process being improved by adding an analysis of the subsequent new exploration video, localizing in the subsequent or new exploration video the same specific point of interest in the body of the explored tagged explored subject, and adding the analysis in the same location on the synchronized subsequent new exploration video, a superimposition of the virtual tags, the same point of interest detection algorithm.

19. The method according to claim 9, wherein the exploration with the flexible endoscope is performed in a tubular organ of a human subject.

20. The method according to claim 9, wherein at least two markers, whose positions can be recorded with the end tip tracking device or system or a marker tracking system separate from the end tip tracking device or system, are previously placed on given anatomical locations on the subject, said locations depending on the explored tubular organ and not undergoing noticeable deformation or displacement when the subject changes position, are used to provide referential points in the previous and subsequent explorations, together with at least one other internal easily identifiable anatomical point.

21. The method according to claim 20, wherein the referential points are used to define and attach a frame or referential to the subject in the first and subsequent explorations.

22. The method according to claim 9, wherein, during the first or previous exploration, a limited number of images are recorded or selected, which contain relevant information, marked or tagged, and wherein, during the subsequent exploration, the video image processing and synchronizing is performed, and guidance information provided, only when the current or live endoscope position is close to the position associated with images containing the relevant information.

23. The method according to claim 9, wherein, when a tubular organ is explored, an image processing is performed which analyzes a lumen position in the video image at a time t during the subsequent exploration and selects the image from the previous or reference exploration associated to a position close to the subsequent live position with a similar lumen position.

24. The method according to claim 9, wherein, when the explored organ is a colon, three points or parts of the colon which are attached to an abdominal wall are used as fixed reference points or locations, the reaching of a target during a subsequent exploration being performed through backward motion.

25. The method according to claim 9, wherein the orientation of the tip of the flexible endoscope is recorded, and exploited, in addition to its 3D position, by the end tip tracking device or system, to evaluate the rotation difference of the endoscope orientation between the reference and the subsequent exploration.

26. The method according to claim 9, wherein precise relocalization of the tip of the flexible endoscope is performed through two consecutive operational steps:

a gross localization, by performing an approximate positioning of the tip of the flexible endoscope close to a reference point or position determined in a previously-conducted procedure; and a fine positioning, by referring to a mapping of a target site or points, taken during a previous procedure onto the video images in the subsequent or current exploration.

* * * * *